United States Patent [19]

O'Donnell

[11] Patent Number: 5,225,675
[45] Date of Patent: Jul. 6, 1993

[54] METHOD OF MONITORING REMOVAL OF METAL TREATMENT SOLUTIONS

[75] Inventor: David B. O'Donnell, Huntington, W. Va.

[73] Assignee: Inco Alloys International, Inc., Huntington, W. Va.

[21] Appl. No.: 824,169

[22] Filed: Jan. 22, 1992

[51] Int. Cl.$^5$ .............................................. G01N 21/64
[52] U.S. Cl. .................. 250/302; 250/459.1; 250/461.1; 134/113
[58] Field of Search ................. 250/302, 459.1, 461.1, 250/458.1; 134/113

[56] References Cited

U.S. PATENT DOCUMENTS

| | | | |
|---|---|---|---|
| 26,888 | 5/1870 | Alburger | 252/301.2 |
| 2,267,758 | 12/1941 | Sell | 250/71 |
| 2,600,221 | 6/1952 | Domingo | 250/302 |
| 3,341,705 | 9/1967 | Alburger | 250/302 |
| 4,327,120 | 4/1982 | Siemers et al. | 427/34 |
| 4,876,206 | 11/1989 | Sayer | 250/302 |
| 4,956,558 | 9/1990 | Batishko et al. | 250/461.1 |
| 5,001,353 | 3/1991 | Odake et al. | 250/461.1 |

FOREIGN PATENT DOCUMENTS

| | | | |
|---|---|---|---|
| 2949254 | 6/1981 | Fed. Rep. of Germany | 250/302 |
| 86743 | 5/1982 | Japan | 250/461.1 |
| 117434 | 6/1986 | Japan | 250/302 |
| 439737 | 11/1974 | U.S.S.R. | 250/302 |

*Primary Examiner*—Carolyn E. Fields
*Attorney, Agent, or Firm*—Blake T. Biederman; Edward A. Steen

[57] ABSTRACT

The invention provides a method of improving cleaning operations for metals. A fluorescent dye is introduced into metal treatment solution and the surface of a metal product is treated with the treatment solution. The metal product with the treatment solution on its surface is worked to deform the metal product. The treatment solution is removed from the surface of the metal product to clean the metal product. The cleaned metal product is illuminated with excitation energy capable of stimulating fluorescence in the fluorescent dye. Fluorescence of the fluorescent dye is optically monitored to determine effectiveness of the removing step.

12 Claims, No Drawings

METHOD OF MONITORING REMOVAL OF METAL TREATMENT SOLUTIONS

FIELD OF INVENTION

The invention provides a method of monitoring application and removal of solutions used in treating metal products.

BACKGROUND OF THE ART AND PROBLEM

Fluorescent dyes have historically been used in a variety of commercial applications. Fluorescent dyes are commercially used as brighteners for white paper, laundry detergents and white polyvinyl chloride pipe. Fluorescent inks are often used as an "invisible ink" to facilitate cutting and sowing of fabric in the garment industry. Fluorescent dye has also been used to identify sources of water, oil and gasoline. The electronics industry has used fluorescent dye technology to automate and control inspection of thin coatings. Fluorescent tracers have also been used to ensure removal of corrosive fluxes arising from soldering and to locate glue smudges before staining wood furniture.

Fluorescent dyes have long been used as a nondestructive method of locating surface cracks in metals. To locate surface cracks, a solution containing a fluorescent dye is first applied to a metal surface. The fluorescence dye is then wiped from the metal surface leaving fluorescent dye in microcracks. An ultra violet light source is then used to locate microcracks by exciting the fluorescent dye within microcracks. The excited dye fluoresces to produce visible light within microcracks not visible by unaided eyesight.

Weldable materials such as filler metals and strip welded into tubing are highly sensitive to residues remaining from metal processing operations. The cleanliness requirements for good weldability are not visually determinable. An extremely small amount of lubricant left on a filler metal after a cleaning operation may cause a filler metal to lose its welding characteristics. Thus, cleaning operations for weldable materials are extremely important. An example of the importance of cleaning filler metal is illustrated in U.S. Pat. No. 4,763,677 which discloses a multistage ultrasonic cleaning device.

The present state of the art for monitoring cleanliness of filler metals has not changed in over forty years. There are essentially two methods of determining whether a filler metal is sufficiently clean for obtaining acceptable welding characteristics. The first method is to weld with a sample of the material to verify welding performance and use radiographic inspection or other methods to evaluate porosity. The second method is to remove a representative short section of filler metal and weigh the removed material as accurately as possible to provide an initial weight. Then the representative wire is treated with a strong base to remove any residue from the filler metal, dried and weighed to determine a final weight. The difference between initial and final weight is used to determine whether the amount of residue on the filler metal is acceptable.

Problems with state of the art monitoring of filler metal cleaning include inaccuracy and delay. Inaccuracy arises from measuring only a small portion (one meter) of a wire that may be a few kilometers long and from the relatively high level of error arising from measuring techniques. The delay problem arises from the fact that filler metals are typically not checked for impurities until after an entire spool of filler metal has been drawn. This delay in time, eliminates any chance of correcting a cleaning operation while filler metal is being processed.

It is an object of this invention to provide a method of increased accuracy for determining amount of treatment solution on the surface of weldable metal product.

It is a further object of this invention to provide a method of monitoring the entire length of a weldable metal product for treatment solution residue.

It is a further object of this invention to provide an immediate method of determining whether treatment solution residue is present.

SUMMARY OF THE INVENTION

The invention provides a method of improving cleaning operations for metals. A fluorescent dye is introduced into metal treatment solution and the surface of a metal product is treated with the treatment solution. The metal product with the treatment solution on its surface is worked to deform the metal product. The treatment solution is removed from the surface of the metal product to clean the metal product. The cleaned metal product is illuminated with excitation energy capable of stimulating fluorescence in the fluorescent dye. Fluorescence of the fluorescent dye is optically monitored to determine effectiveness of the removing step.

DESCRIPTION OF PREFERRED EMBODIMENT

It has been discovered that mixing a fluorescent dye directly into a treatment solution used in metal working provides an improved method of monitoring subsequent metal cleanliness. For purposes of this specification, metal working is defined as any mechanical operation such as drawing, extruding, rolling or swaging which alters shape of a metal without melting the metal. After a cleaning operation, the metal product is illuminated with sufficient energy to fluoresce the fluorescent dye to make treatment solution readily visible. For purposes of this invention, a treatment solution is defined as any lubricant or process agent such as oils, organic solutions, soaps or waxes that are directly applied to a metal surface. Typical, advantageous applications of treatment solutions include drawing lubricants for producing weld wire and rolling lubricants for rolling wire strip.

It is recognized that a fluorescent dye may also be added directly to a lubricant or arc stabilizer that is added to a filler metal to monitor uniformity and quantity of application. Preferably when fluorescent dye is added to a lubricant or arc stabilizer, a fluorescent dye having a different fluorescence wavelength than the fluorescent dye of the treatment solution is used for each ingredient added. Separate fluorometers adjusted to separate wavelengths may then be used to simultaneously monitor for residual treatment solution and deliberate addition of ingredients.

Most preferably, a treatment solution such as a lubricant may be monitored continuously over an entire length of a metal product with a fluorometer. The continuous monitoring over the entire length provides immediate feedback for adjustment of removal or cleaning of treatment solution. A fluorometer set to a predetermined wavelength may be used to produce a signal proportional to amount of treatment solution present. For example, a rolling line may be temporarily shut down when an optical indicator reaches a predetermined level to prevent production of "defective" material. The immediate feedback of cleaning effectiveness will provide an opportunity to maually or automatically adjust a cleaning operation prior to reaching unacceptable residue levels and prevent the production of defective material. Furthermore, continuously monitoring a metal product over an entire length provides an accurate measurement of residue levels over complete lengths of materials. For example, a coil or production lot of filler metal may have a length of 5 km that would be completely checked for excess treatment solution. Most advantageously, continuous recording with a computer is used to create a retrievable record of cleaning effectiveness that may be used for statistical process control of the cleaning operation.

A combination of parameters are used to select a suitable fluorescent dye. For example, a fluorescent dye preferably has a high photon efficiency, low chloride content and a high solubility in the metal treatment solution to be monitored. Three fluorescent dyes (Keystone CL, Keystone PL and Crompton & Knowles Intrawite® OB) were dissolved in mineral oil and checked for photon efficiency. It was found that Keystone PL and Crompton & Knowles Intrawite OB each had similar relatively high photon efficiencies. A 500 ppm concentration of Intrawite OB was determined to be completely soluble in mineral oil at 20° C. A 500 ppm solution of Intrawite OB in mineral oil aged for a week at room temperature without any evidence of slow precipitation. A 1000 ppm concentration of Intrawite OB precipitated as small fibers when cooled below 30° C. A mineral oil based pigment (Oil-Glow 22) appeared to be technically feasible. However, Oil-Glow 22 contained an undesirable red dye and 2.5 wt % Cl. By comparison, Intrawite OB was found to only contain 0.12% Cl which is equivalent to only 0.6 ppm cl in a 500 ppm solution of fluorescent dye. Fluorescent dyes added to a treatment solution most preferably contain less than 10 ppm Cl to minimize adverse effects of chloride ion.

A technical data bulletin by Compton & Knowles Corporation lists the following general properties of Intrawite® OB:

| GENERAL PROPERTIES | |
|---|---|
| Chemical nature | Benzoxazole Thiophene |
| Physical form | Yellow-green powder |
| Ionic nature | Nonionic |
| Apparent bulk density (kg/liter) | 0.365 |
| Specific gravity | 1.27 |
| Melting point | 200°–201° C. |

EXAMPLE 1

A 500 ppm concentration of Intrawite OB fluorescent dye was added to a mineral oil lubricant and cooling solution used during cold rolling of sheet metal or narrow strip into tubing. The 500 ppm concentration remained soluble in the mineral oil for 2 weeks without any signs of precipitation. The fluorescent dye did not have any adverse affects upon cold rolling operations. Furthermore, the solution traveled through a 10 μm particulate filter and a bentonite filter without any problems. An ultraviolet light was used to illuminate the strip after washing. The illumination continuously verified that the washing operation was operating successfully for at least 2 weeks. Visual monitoring of the heater strip cleaning operation provided for an immediate indication whenever the cleaning operation was malfunctioning. Upon any indication of cleaning operations malfunctioning, the cleaning operation may be immediately adjusted to ensure the benefits of high cleanliness. High cleanliness of heater strip provides for improved high speed weldability and increased annealing furnace life by reducing the amount of volatile residue forming components entering an annealing furnace.

EXAMPLE 2

A sodium stearate drawing lubrication mixture was mixed with 500 ppm of Intrawite OB. The Intrawite OB was added and mixed with stearate soap powder which eliminated any solubility problems. The sodium stearate solution was added to the final draw operation used to produce a 0.114 cm diameter INCONEL® Filler Metal 82. The dye was highly visible upon ultra violet light activation. The fluorescent dye did not have any adverse effects upon drawing operations. By ultra violet radiation, it was discovered that two areas of the cleaner were not operating properly due to clogged piping. The piping was cleared and the cleaning operation was subsequently found to clean effectively. After repair, with the ultrasonic cleaners functioning properly, no dye was visible on the weld wire.

The invention provides several advantages. The invention provides an accurate method to monitor an entire length of a metal product for treatment solution following a cleaning operation. The use of a fluorescent dye also provides an immediate indication of when a cleaning solution begins to lose cleaning effectiveness. This information of ineffective cleaning may be used to temporarily stop a production line for repairs or be used to automatically adjust a cleaning operation for maintaining acceptable cleaning power.

The effectiveness of a coating step on a cleaned weldable product can be determined by coating with a treatment ingredient containing a fluorescent dye that fluoresces at a different wavelength than the fluorescent dye that is removable by the cleaning step. The coated weldable metal product is then illuminated with excitation energy capable of stimulating fluorescence in the coating fluorescent dye, and the fluorescence is optically monitored to determine effectiveness of the coating step.

While in accordance with the provisions of the statute, there is illustrated and described herein specific embodiments of the invention. Those skilled in the art will understand that changes may be made in the form of the invention covered by the claims and the certain features of the invention may sometimes be used to advantage without a corresponding use of the other features.

The embodiments of the invention in which an exclusive property or privilege is claimed are defined as follows:

1. A method of improving cleaning operations for improving weldability of metals comprising the steps of:
   a) introducing a fluorescent dye into a lubricant and treating a surface of a weldable metal product with said lubricant;
   b) mechanically working said weldable metal product with said lubricant and said fluorescent dye on said surface of said weldable metal product to deform said weldable metal product with said lubricant being for lubricating said mechanical working;

c) removing said lubricant and said fluorescent dye from said surface of said weldable metal product to clean said weldable metal product;

d) illuminating the cleaned weldable metal product with excitation energy capable of stimulating fluorescence in said fluorescent dye; and e) optically monitoring fluorescence of said fluorescent dye on said weldable metal product to determine effectiveness of said removing step.

2. The method of claim 1 including the additional step of:

f) adjusting said removing of lubricant upon said monitoring fluorescence of said fluorescent dye indicating a predetermined level of lubricant remaining.

3. The method of claim 1 including the additional step of:

g) continuously recording amount of said fluorescence of said fluorescent dye to create a retrievable record to determine amount of lubricant remaining on a complete length of said weldable metal product.

4. The method of claim 1 wherein said monitoring fluorescence of said fluorescent dye includes illuminating said weldable metal product with ultraviolet light and using a fluorometer to determine whether excess lubricant remains on the surface of said weldable metal.

5. The method of claim 1 wherein said weldable metal product treated is selected from the group consisting of filler metal, weldable metal strip and wire for use in coated electrodes.

6. A method of treating welding materials for improving weldability of metals comprising the steps of:

a) introducing a removable fluorescent dye into a lubricant and treating a surface of a weldable metal product with said lubricant;

b) drawing said weldable metal product with said lubricant and said fluorescent dye on said surface of said weldable metal product to deform said weldable metal product into weld wire with said lubricant being for lubricating said drawing;

c) removing said lubricant and said fluorescent dye from said surface of said weld wire to clean said weld wire;

d) illuminating the cleaned weld wire with excitation energy capable of stimulating fluorescence in said removable fluorescent dye;

e) optically monitoring fluorescence of said removable fluorescent dye on said weld wire to determine effectiveness of said removing step and to provide for adjusting of said removing of lubricant upon said monitoring fluorescence of said removable fluorescent dye indicating an excess level of lubricant remaining.

7. The method of claim 6 including the additional step of:

f) continuously recording amount of said fluorescence of said removable fluorescent dye to create a retrievable record to determine amount of lubricant remaining on a complete length of said weldable metal product.

8. The method of claim 6 including the additional steps of:

g) coating the cleaned weldable product with a treatment ingredient, said treatment ingredient containing a coating fluorescent dye that fluoresces at a different wavelength than said removable fluorescent dye, h) illuminating said coated weldable metal product with excitation energy capable of stimulating fluorescence in said coating fluorescent dye, and i) optically monitoring fluorescence of said coating fluorescent dye on said weldable metal product to determine effectiveness of said coating step.

9. The method of claim 6 wherein said monitoring fluorescence of said removable fluorescent dye includes illuminating said weldable metal product with ultraviolet light and using a fluorometer to determine whether excess lubricant remains on the surface of said weldable metal.

10. The method of claim 6 wherein said weldable metal product treated is selected from the group consisting of filler metal, weldable metal strip and wire for use in coated electrodes.

11. The method of claim 6 wherein said drawing includes using a lubricant selected from the group consisting of oils, organic solutions, soaps and waxes.

12. The method of claim 6 wherein said drawing includes using a stearic acid solution.

* * * * *